United States Patent [19]

Mallion

[11] Patent Number: 5,554,613
[45] Date of Patent: Sep. 10, 1996

[54] HETEROCYCLIC DERIVATIVES

[75] Inventor: Keith B. Mallion, Knutsford, England

[73] Assignee: Zeneca Limited, London, England

[21] Appl. No.: 190,073

[22] PCT Filed: Jun. 2, 1993

[86] PCT No.: PCT/GB93/01165

§ 371 Date: Jun. 9, 1994

§ 102(e) Date: Jun. 9, 1994

[87] PCT Pub. No.: WO93/24486

PCT Pub. Date: Dec. 9, 1993

[30] Foreign Application Priority Data

Jun. 4, 1992 [GB] United Kingdom .................. 9211796

[51] Int. Cl.⁶ ............... C07D 401/10; C07D 413/10; A61K 31/495; A61K 31/44

[52] U.S. Cl. ............... 514/253; 514/255; 514/256; 514/305; 544/238; 544/332; 544/359; 546/133

[58] Field of Search .............. 546/133; 544/238, 544/359, 332; 514/253, 255, 256, 305

[56] References Cited

U.S. PATENT DOCUMENTS

| | | | |
|---|---|---|---|
| 3,405,134 | 10/1968 | Judd | 546/133 |
| 3,534,053 | 10/1970 | Sallay et al. | 546/133 |
| 3,586,694 | 6/1971 | Shen et al. | 548/304.4 |
| 3,655,675 | 4/1972 | Carabateas | 546/224 |
| 3,679,690 | 7/1972 | Carabateas | 546/316 |
| 3,725,410 | 4/1973 | Potoski et al. | 544/127 |
| 3,763,168 | 10/1973 | Carabateas | 546/224 |
| 3,857,848 | 12/1974 | Mauvernay et al. | 546/133 |
| 4,038,402 | 7/1977 | Kaminka et al. | 514/305 |
| 4,224,332 | 9/1980 | Gueremy et al. | 546/133 |
| 4,599,344 | 7/1986 | Morgan | 514/305 |
| 5,135,935 | 8/1992 | Alberts et al. | 514/305 |
| 5,242,914 | 9/1993 | Kawamoto et al. | 514/210 |
| 5,286,864 | 2/1994 | Walther et al. | 546/133 |
| 5,385,912 | 1/1995 | Neuenschwander et al. | 514/305 |

FOREIGN PATENT DOCUMENTS

| | | |
|---|---|---|
| 77130/91 | 11/1991 | Australia . |
| 1014958 | 8/1977 | Canada . |
| 0307142 | 3/1989 | European Pat. Off. . |
| 0316718 | 5/1989 | European Pat. Off. . |
| 0322182 | 6/1989 | European Pat. Off. . |
| 0328200 | 8/1989 | European Pat. Off. . |
| 0330826 | 9/1989 | European Pat. Off. . |
| 0337637 | 10/1989 | European Pat. Off. . |
| 0370415 | 5/1990 | European Pat. Off. . |
| 0412797 | 2/1991 | European Pat. Off. . |
| 0458214 | 11/1991 | European Pat. Off. . |
| 0497415 | 8/1992 | European Pat. Off. . |
| 2323303 | 12/1973 | Germany . |
| 2502916 | 11/1975 | Germany . |
| 4116582 | 11/1991 | Germany . |
| 1416958 | 12/1975 | United Kingdom . |
| 2169292 | 7/1986 | United Kingdom . |
| 92/15579 | 9/1992 | WIPO . |
| 9309115 | 5/1993 | WIPO ............................ 546/133 |
| 93/15073 | 8/1993 | WIPO . |
| 93/16048 | 8/1993 | WIPO . |

*Primary Examiner*—Alan L. Rotman
*Attorney, Agent, or Firm*—Cushman Darby & Cushman, L.L.P.

[57] ABSTRACT

Quinuclidine derivatives of formula I, and their pharmaceutically acceptable salts,

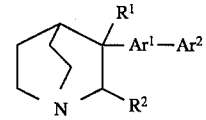

in which $R^1$ is hydrogen or hydroxy; $R^2$ is hydrogen; or $R^1$ and $R^2$ are joined together so that $CR^1$-$CR^2$ is a double bond; $Ar^1$ is a phenylene moiety; $Ar^2$ is a 6-membered heteroaryl moiety containing one or two nitrogen atoms; and wherein one or both of $Ar^1$ and $Ar^2$ may optionally bear one or more substituents such as halogeno, hydroxy, amino, nitro, cyano, carboxy, carbamoyl, alkyl, alkenyl, alkynyl, alkoxy, alkylamino, di-alkylamino, N-alkylcarbamoyl, di-N, N-alkylcarbamoyl, alkoxycarbonyl, alkylthio, alkylsulphinyl, alkylsulphonyl, halogenoalkyl, alkanoylamino, alkylenedioxy, alkanoyl and oxime derivatives thereof and O-alkyl ethers of said oxime derivatives; inhibit squalene synthase and are therefore useful in treating treating diseases and medical conditions where inhibition of squalene synthase is desirable, for example in treating hypercholesterolemia and atherosclerosis. Processes for the preparation of these derivatives and pharmaceutical compositions containing them are also referred to as well as their use in medicine.

13 Claims, No Drawings

5,554,613

HETEROCYCLIC DERIVATIVES

This application is a 371 of PCT/GB 93/01165 filed Jun. 02, 1993.

FIELD OF INVENTION

This invention concerns heterocyclic derivatives which are useful in inhibiting squalene synthase, processes for their preparation and pharmaceutical compositions containing them. The present invention is also concerned with methods of using such heterocyclic derivatives in treating diseases and medical conditions where inhibition of squalene synthase is desirable, for example in treating diseases or medical conditions such as hypercholesterolemia and atherosclerosis.

BACKGROUND TO INVENTION

Several different classes of compounds have been reported to possess the capability of being able to lower cholesterol levels in blood plasma. For example agents which inhibit the enzyme HMG CoA reductase, which is essential for the production of cholesterol, have been reported to reduce levels of serum cholesterol. Illustrative of this class of compounds is the HMG CoA reductase inhibitor known as lovastatin which is disclosed in U.S. Pat. No. 4,231,938. Other agents which are reported to lower serum cholesterol include those which act by complexing with bile acids in the intestinal system and which are hence termed "bile acid sequestrants". It is believed that many of such agents act by sequestering bile acids within the intestinal tract. This results in a lowering of the levels of bile acid circulating in the enteroheptatic system and promoting replacement of bile acids by synthesis in the liver from cholesterol, which results in an upregulation of the heptatic LDL receptor, and thus in a lowering of circulating blood cholesterol levels.

Squalene synthase is a microsomal enzyme which catalyses the first committed step of cholesterol biosynthesis. Two molecules of farnesyl pyrophosphate (FPP) are condensed in the presence of the reduced form of nicotinamide adenine dinucleotide phosphate (NADPH) to form squalene. The inhibition of this committed step to cholesterol should leave unhindered biosynthetic pathways to ubiquinone, dolichol and isopentenyl t-RNA. Elevated cholesterol levels are known to be one of the main risk factors for ischaemic cardiovacsular disease. Thus, an agent which inhibits squalene synthase should be useful in treating diseases and medical conditions in which a reduction in the levels of cholesterol is desirable, for example hypercholesterolemia and atherosclerosis.

Thus far, the design of squalene synthase inhibitors has concentrated on the preparation of analogues of the substrate farnesyl pyrophosphate (FPP), and hence on compounds which contain phosphorus groups. For example, the preparation of phosphorous-containing squalene synthase inhibitors is reported in published European Patent Application No. 409,181; and the preparation of isoprenoid (phosphinylmethyl)phosphonates as inhibitors of squalene synthase is reported by Biller et al, J. Med. Chem., 1988, 31, 1869.

Quinuclidine derivatives which inhibit squalene synthase have been reported in U.S. Pat. No. 5,135,935 and WO 92/15579.

DISCLOSURE OF INVENTION

The present invention is based on the discovery that certain heterocyclic derivatives are inhibitors of squalene synthase, and are hence useful in treating diseases and medical conditions in which inhibition of squalene synthase is desirable.

According to the present invention there is provided a compound of formula I (formula set out hereinafter together with the other chemical formulae referred to herein), or a pharmaceutically acceptable salt thereof, wherein:

$R^1$ is hydrogen or hydroxy;

$R^2$ is hydrogen; or $R^1$ and $R^2$ are joined together so that $CR^1$—$CR^2$ is a double bond;

$Ar^1$ is a phenylene moiety;

$Ar^2$ is a 6-membered heteroaryl moiety containing one or two nitrogen atoms;

and wherein one or both of $Ar^1$ and $Ar^2$ may optionally bear one or more substituents independently selected from halogeno, hydroxy, amino, nitro, cyano, carboxy, carbamoyl, (1–6C)alkyl, (2–6C)alkenyl, (2–6C)alkynyl, (1–6C)alkoxy, (1–6C)alkylamino, di-[(1–6C)alkyl]amino N-(1–6C)alkylcarbamoyl, di-N,N-[(1–6C)alkyl]carbamoyl, (1–6C)alkoxycarbonyl, (1–6C)alkylthio, (1–6C)alkylsulphinyl, (1–6C)alkylsulphonyl, halogeno(1–6C)alkyl, (1–6C)alkanoylamino,(1–4C)alkylenedioxy, (1–6C)alkanoyl and oxime derivatives thereof and 0-(1–6C)alkyl ethers of said oxime derivatives.

It will be understood that when formula I compounds contain a chiral centre, the compounds of the invention may exist in, and be isolated in, optically active or racemic form. The invention includes any optically active or racemic form of a compound of formula I which possesses the beneficial pharmacological effect of inhibiting squalene synthase. The synthesis of optically active forms may be carried out by standard techniques of organic chemistry well known in the art, for example by, resolution of a racemic form, by synthesis from optically active starting materials or by asymmetric synthesis.

It will also be understood that, insofar as certain of the compounds of the formula I may exhibit the phenomenon of tautomerism, for example a compound of formula I in which $Ar^2$ bears a hydroxy substituent, the present invention includes any tautomeric form of a compound of formula I which possesses the beneficial pharmacological effect of inhibiting squalene synthase.

It is also to be understood that generic terms such as "alkyl" include both the straight chain and branched chain groups such as butyl and tert-butyl. However, when a specific term such as "butyl" is used, it is specific for the straight chain or "normal" butyl group, branched chain isomers such as "t-butyl" being referred to specifically when intended.

It will be appreciated that when $R^1$ and $R^2$ are joined so that $CR^1$—$CR^2$ is a double bond, the quinuclidine ring in formula I will comprise the 2,3-dehydroquinuclidine moiety shown in formula Ia.

It will also be appreciated that oxime derivatives of the (1–6C)alkanoyl group will comprise aldoximes and ketoximes of formula —C(Ra)=NOH (Ra is H or alkyl), and the O-alkyl ethers of these oximes will have the formula —C(Ra)=NORb (Ra is H or alkyl, and Rb is alkyl).

$Ar^2$, the 6-membered heteroaryl moiety containing one or two nitrogen atoms, will comprise an unsaturated 6-membered ring which contains one or two nitrogen atoms as ring atoms, and may be attached to $Ar^1$ through any available ring carbon atom.

Suitable values for $Ar^2$ include pyridyl, pyrimidinyl, pyrazinyl and pyridazinyl.

Suitable values for $Ar^1$, the phenylene moiety, include 1,2-phenylene; 1,3-phenylene and 1,4-phenylene.

A particular value for an optional substituent which may be present on $Ar^1$ or $Ar^2$ is, for example,

| | |
|---|---|
| for alkyl; | (1–4C)alkyl, such as methyl, ethyl, propyl, isopropyl, butyl, isobutyl or sec-butyl; |
| for alkenyl; | (2–4C)alkenyl, such as allyl, prop-1-enyl, but-2-enyl or 2-methyl-2-propenyl; |
| for alkynyl; | (2–4C)alkynyl, such as prop-2-ynyl or but-2-ynyl; |
| for alkoxy; | (1–4C)alkoxy, such as methoxy, ethoxy, propoxy, isopropoxy or butoxy; |
| for alkylamino; | (1–4C)alkylamino, such as methylamino, ethylamino, propylamino or butylamino; |
| for di-alkylamino; | dimethylamino, diethylamino, methylpropylamino or dipropylamino; |
| for alkylcarbamoyl; | N-methylcarbamoyl, N-ethylcarbamoyl or N-propylcarbamoyl; |
| for di-alkylcarbamoyl; | N,N-dimethylcarbamoyl or N,N-diethylcarbamoyl; |
| for alkoxycarbonyl; | methoxycarbonyl, ethoxycarbonyl or propoxycarbonyl; |
| for alkylthio; | methylthio, ethylthio, propylthio, isopropylthio or butylthio; |
| for alkylsulphinyl; | methylsulphinyl, ethylsulphinyl, propylsulphinyl, isopropylsulphinyl or butylsulphinyl; |
| for alkylsulphonyl; | methylsulphonyl, ethylsulphonyl, propylsulphonyl, isoproylsulphonyl or butylsulphonyl; |
| for halogeno; | fluoro, chloro, bromo or iodo; |
| for halogenoalkyl; | halogenoalkyl containing one, two or three halo groups selected from fluoro, chloro, bromo and iodo and an alkyl group selected from methyl, ethyl, propyl, iso-propyl, butyl, iso-butyl and sec-butyl, thus particular values will include trifluoromethyl, difluoromethyl and fluoromethyl; |
| for alkylenedioxy; | methylenedioxy or ethylenedioxy; |
| for alkanoylamino; | formamido, acetamido, propionamido, iso-propionamido, butyramido or iso-butyramido; |
| for alkanoyl; | formyl, acetyl, propionyl or butyryl; |
| for 0-(1–6C)alkyl ethers of alkanoyl oximes | methyl, ethyl, propyl, isopropyl and butyl ethers of said oximes; |

A particular value for $Ar^1$ is, for example, 1,3-phenylene or 1,4-phenylene.

In general, it is preferred that $Ar^1$ is optionally unsubstituted or substituted by one, two or three substituents independently selected from those mentioned above; and that $Ar^2$ is optionally unsubstituted or substituted by one, two or three substituents from those mentioned above. In particular, one or both of $Ar^1$ and $Ar^2$ may optionally bear one or two substituents.

In a particular embodiment one or both of $Ar^1$ and $Ar^2$ may optionally bear one or more substituents independently selected from halogeno, hydroxy, amino, nitro, cyano, carboxy, carbamoyl, (1–6C)alkyl, (1–6C)alkoxy, (1–6C)alkylamino, di-[(1–6C)alkyl]amino, (1–6C)alkylcarbamoyl, di-[(1–6C)alkyl]carbamoyl, (1–6C)alkoxycarbonyl, (1–6C)alkylthio, (1–6C)alkylsulphinyl, (1–6C)alkylsulphonyl, halogeno (1–6C)alkyl and (1–6C)alkanoylamino.

In a further embodiment one or both of $Ar^1$ and $Ar^2$ may optionally bear one or more substituents independently selected from halogeno, hydroxy, amino, nitro, cyano, carboxy, carbamoyl, (1–6C)alkyl, (1–6C)alkoxy, (1–6C)alkylamino, di-[(1–6C)alkyl]carbamoyl, (1–6C)alkoxycarbonyl, (1–6C)alkylthio, (1–6C)alkylsulphinyl, (1–6C)alkylsulphonyl, halogeno (1–6C)alkyl and (1–6C)alkanoylamino.

In a further embodiment, one or both of $Ar^1$ and $Ar^2$ may optionally bear one or more substituents selected from halogeno, hydroxy, nitro, (1–6C)alkyl, (1–6C)alkoxy, (1–6C)alkylthio, (1–6C)alkylsulphinyl, (1–6C)alkylsulphonyl and halogeno-(1–6C)alkyl.

In general, it is preferred that $Ar^1$ is 1,4-phenylene.

In general, it is preferred that $R^1$ is hydroxy and $R^2$ is hydrogen.

In general, it is preferred that $Ar^2$ is pyridyl.

Specific values for $Ar^2$ include, for example:

for pyridyl; 2-pyridyl, 3-pyridyl or 4-pyridyl;

for pyrimidinyl; 2-pyrimidinyl or 5-pyrimidinyl;

for pyrazinyl; 2-pyrazinyl; and for pyridazinyl; 3-pyridazinyl;

(which values for $Ar^2$ may be unsubstituted or may optionally bear one or more substituents as herein defined for $Ar^2$).

Specific values for substituents which may optionally be present on $Ar^2$ are alkyl (such as methyl) and alkoxycarbonyl (such as ethoxycarbonyl).

In a specific embodiment $Ar^1$ and $Ar^2$ are both unsubstituted.

In a further specific embodiment $Ar^1$ is unsubstituted and $Ar^2$ is unsubstituted or bears one or two substitutents independently selected from those hereinbefore defined.

Particular groups of compounds of interest include those in which:

(a) $Ar^2$ is pyridyl (especially 3-pyridyl or 4-pyridyl);

(b) $Ar^2$ is pyrimidinyl (especially 2-pyrimidinyl or 5-pyrimidinyl);

(c) $Ar^2$ is pyrazinyl (especially 2-pyrazinyl); or (d) $Ar^2$ is pyridazinyl (especially 3-pyridazinyl);

and wherein in each group $R^1$ is hydroxyl $R^2$ is hydrogen; $Ar^1$ is 1,4-phenylene; and wherein one or both of $Ar^1$ and $Ar^2$ may optionally bear one or more substituents independently selected from halogeno, hydroxy, amino, nitro, cyano, carboxy, carbamoyl, (1–6C)alkyl, (2–6C)alkenyl, (2–6C)alkynyl, (1–6C)alkoxy, (1–6C)alkylamino, di-[(1–6C)alkyl]amino N-(1–6C)alkylcarbamoyl, di-N,N-[(1–6C)alkyl]carbamoyl, (1–6C)alkoxycarbonyl, (1–6C)alkylthio, (1–6C)alkylsulphinyl, (1–6C)alkylsulphonyl, halogeno(1–6C)alkyl, (1–6C)alkanoylamino, (1–4C)alkylenedioxy, (1–6C)alkanoyl and oxime derivatives thereof and 0-(1–6C)alkyl ethers of said oxime derivatives.

Particular, preferred and specific values inlcude the appropriate values mentioned above.

In one embodiment of the present invention, $R^1$ and $R^2$ are both hydrogen; and $Ar^1$ and $Ar^2$ have any of the meanings defined above.

In a further embodiment of the present invention, $R^1$ is hydroxyl $R^2$ is hydrogen; and $Ar^1$ and $Ar^2$ have any of the meanings defined above.

In a further embodiment of the present invention, $R^1$ and $R^2$ are joined together so that $CR^1$—$CR^2$ is a double bond; and $Ar^1$ and $Ar^2$ have any of the meanings defined above.

In one embodiment of the present invention there is provided a compound of formula I, or a pharmaceutically acceptable salt thereof, wherein:

$R^1$ is hydrogen or hydroxyl $R^2$ is hydrogen; or $R^1$ and $R^2$ are joined together so that $CR^1$–$CR^2$ is a double bond;

$Ar^1$ is a phenylene moiety;

$Ar^2$ is a 6-membered heteroaryl moiety containing one or two nitrogen atoms;

and wherein one or both of $Ar^1$ and $Ar^2$ may optionally bear one or more substituents independently selected from halogeno, hydroxy, amino, nitro, cyano, carboxy, carbamoyl, (1–6C)alkyl, (1–6C)alkoxy, (1–6C)alkylamino, di-[(1–6C)alkyl]carbamoyl, (1–6C)alkoxycarbonyl, (1–6C)alkylthio, (1–6C)alkylsulphinyl, (1–6C)alkylsulphonyl, halogeno (1–6C)alkyl and (1–6C)alkanoylamino.

Particular, preferred and specific values inlcude the appropriate values mentioned above.

In a preferred embodiment $R^1$ is hydroxyl $R^2$ is hydrogen; $Ar^1$ is 1,4-phenylene; $Ar^2$ is a 6-membered heteroaryl moiety containing one or two nitrogen atoms;
and wherein one or both of $Ar^1$ and $Ar^2$ may optionally bear one or more substituents independently selected from halogeno, hydroxy, amino, nitro, cyano, carboxy, carbamoyl, (1–6C)alkyl, (2–6C)alkenyl, (2–6C)alkynyl, (1–6C)alkoxy, (1–6C)alkylamino, di-[(1–6C)alkyl]amino N-(1–6C)alkylcarbamoyl, di-N,N-[(1–6C)alkyl]carbamoyl, (1–6C)alkoxycarbonyl, (1–6C)alkylthio, (1–6C)alkylsulphinyl, (1–6C)alkylsulphonyl, halogeno(1–6C)alkyl, (1–6C)alkanoylamino, (1–4C)alkylenedioxy, (1–6C)alkanoyl and oxime derivatives thereof and 0-(1–6C)alkyl ethers of said oxime derivatives.

Particular, preferred and specific values inlcude the appropriate values mentioned above.

In a further embodiment $R^1$ is hydrogen or hydroxy; $R^2$ is hydrogen; or $R^1$ and $R^2$ are joined together so that $CR^1$—$CR^2$ is a double bond; $Ar^1$ is a 1,4-phenylene moiety; $Ar^2$ is pyridyl (especially 2-pyridyl, 3-pyridyl or 4-pyridyl), pyrimidinyl (especially 2-pyrimidinyl or 5-pyrimidinyl), pyrazinyl (especially 2-pyrazinyl), or pyridazinyl (especially 3-pyridazinyl); and wherein one or both of $Ar^1$ and $Ar^2$ may optionally bear one or more substituents independently selected from halogeno, hydroxy, amino, nitro, cyano, carboxy, carbamoyl, (1–6C)alkyl, (2–6C)alkenyl, (2–6C)alkynyl, (1–6C)alkoxy, (1–6C)alkylamino, di-[(1–6C)alkyl] amino N-(1–6C)alkylcarbamoyl, di-N,N-[(1–6C)alkyl] carbamoyl, (1–6C)alkoxycarbonyl, (1–6C)alkylthio, (1–6C)alkylsulphinyl, (1–6C)alkylsulphonyl, halogeno(1–6C)alkyl, (1–6C)alkanoylamino, (1–4C)alkylenedioxy, (1–6C)alkanoyl and oxime derivatives thereof and 0-(1–6C)alkyl ethers of said oxime derivatives.

Particular, preferred and specific values inlcude the appropriate values mentioned above.

In a further preferred embodiment of the present invention there is provided a compound of formula I, or a pharmaceutically acceptable salt thereof, wherein:

$R^1$ is hydrogen or hydroxyl $R^2$ is hydrogen; or $R^1$ and $R^2$ are joined together so that $CR^1$—$CR^2$ is a double bond;

$Ar^1$ is a 1,4-phenylene moiety;

$Ar^2$ is a pyridyl, pyrimidinyl, pyrazinyl or pyridazinyl moiety; and wherein one or both of $Ar^1$ and $Ar^2$ may optionally bear one, two or three substituents selected from halogeno, hydroxy, amino, nitro, cyano, carboxy, carbamoyl, (1–6C)alkyl, (1–6C)alkoxy, (1–6C)alkylamino, di-[(1–6C)alkyl]carbamoyl, (1–6C)alkoxycarbonyl, (1–6C)alkylthio, (1–6C)alkylsulphinyl, (1–6C)alkylsulphonyl, halogeno (1–6C)alkyl and (1–6C)alkanoylamino.

Particular, preferred and specific values are the appropriate values mentioned above.

In a further preferred embodiment of the present invention there is provided a compound of formula I, or a pharmaceutically acceptable salt thereof, wherein:

$R^1$ is hydrogen or hydroxy;

$R^2$ is hydrogen; or $R^1$ and $R^2$ are joined together so that $CR^1$—$CR^2$ is a double bond;

$Ar^1$ is a 1,4-phenylene moiety; and $Ar^2$ is a pyridyl group; and
wherein one or both of $Ar^1$ and $Ar^2$ may optionally bear one, two or three substituents selected from halogeno, hydroxy, amino, nitro, cyano, carboxy, carbamoyl, (1–6C)alkyl, (1–6C)alkoxy, (1–6C)alkylamino, di-[(1–6C)alkyl]carbamoyl, (1–6C)alkoxycarbonyl, (1–6C)alkylthio, (1–6C)alkylsulphinyl, (1–6C)alkylsulphonyl, halogeno (1–6C)alkyl and (1–6C)alkanoylamino.

Particular, preferred and specific values are the appropriate values mentioned above.

In a specific embodiment of the present invention there is provided a compound of formula I, or a pharmaceutically acceptable salt thereof, wherein;

$R^1$ is hydroxy; $R^2$ is hydrogen; $Ar^1$ is 1,4-phenylene and $Ar^2$ is pyridyl.

Compounds of the invention which are of particular interest include the compounds described in the accompanying Examples (and their pharmaceutically-acceptable salts), and are hence provided as a further feature of the present invention.

A suitable pharmaceutically-acceptable salt of the present invention comprises an acid-addition salt derived from an inorganic or organic acid which provides a pharmaceutically-acceptable anion. Thus, examples of salts of the present invention include acid-addition salts with hydrochloric, hydrobromic, nitric, sulphuric, phosphoric, trifluoroacetic, citric, tartaric, succinic, maleic, fumaric or acetic acid. In addition, suitable pharmaceutically-acceptable salts include [where the compound of formula I is sufficiently acidic, for example where the compound of formula I bears an acidic substituent such as carboxy] those formed with a base which affords a pharmaceutically acceptable cation. Suitable bases include an alkali metal salt (such as a sodium or potassium salt), an alkaline earth metal salt (such as a calcium or magnesium salt), an ammonium salt or a salt with an organic base which affords a physiologically-acceptable cation such as a salt with methylamine, dimethylamine, triethylamine, piperidine or morpholine.

The compounds of the present invention may be obtained by standard procedures of organic chemistry already known to be applicable to the preparation of structurally analogous compounds. Such procedures for the preparation of the compounds of formula I, or pharmaceutically acceptable salts thereof, are provided as a further feature of the present invention and are illustrated by the following preferred processes in which the various generic radicals, for example $R^1$, $R^2$, $Ar^1$ and $Ar^2$ have any of the meanings defined hereinbefore, and in which $Ar^1$ and $Ar^2$ may be unsubstituted or substituted as hereinbefore defined.

(a) For those compounds of formula I in which $R^1$ is hydroxy and $R^2$ is hydrogen, reacting a compound of formula II in which M is a metal atom or a derivative thereof, with quinuclidin-3-one.

Suitable values for M include, for example, magnesium and lithium. In the case where M is magnesium it is conveniently present in the form of a derivative such as the group —MgX where X is a halogen atom, such as iodo or bromo, so that the compound of formula II is a "Grignard Reagent". When M is a metal such as lithium, the reaction is generally carried out at a temperature from ambient temperature to −100° C. (conveniently at about −70° C.); and where M is —MgX the reaction is generally carried out at a temperature from ambient to the reflux temperature of the reaction mixture (conveniently at reflux).

The compounds of formula II may be prepared by reacting a compound of formula IIa in which "hal" is a halogeno atom such as iodo or bromo with the appropriate metal. For example in the case where M is the group —MgX, the compound of formula IIa may be reacted with magnesium turnings as is well known in the art. The desired Grignard Reagent may also be prepared by a transmetallation reaction, for example by reaction of a compound of formula IIa with a Grignard Reagent such as MeMgBr. Where M is a metal atom such as lithium, the compound of formula II may be prepared by reaction of a compound of formula IIa with lithium in an inert solvent such as dry ether or tetrahydrofuran at a temperature below 0° C., such as at about −70° C. Alternatively, the compound of formula IIa may be treated with an alkyl lithium compound such as sec-butyl lithium.

The compounds of formula IIa may be prepared from compounds of formula IIb in which "hal" is a halogen atom such as iodo or bromo. The compound of formula IIb is treated with sodium nitrite and concentrated hydrochloric acid with cooling as described in Example 1 part(a) to generate a diazonium salt which is then treated with the heterocyclic compound, $Ar^2$ to give the compound of formula IIa. Positional isomers may be separated using conventional techniques such as column chromatography.

Alternatively, the compounds of formula IIa may be prepared by reaction of the appropriate heteroaryl compound of formula $Ar^1$—X in which X is a leaving group such as halogen (for example, bromo) or trifluoromethanesulphonyloxy, with the appropriate compound of formula IIc in which "hal" is halogen such as bromo and $L^1$ and $L^2$ are suitable ligands such as hydroxy. The reaction will be carried out in the presence of a catalyst such as tetrakis(triphenylphosphine)palladium(0). Suitable reaction conditions are those mentioned in (b) below.

(b) Reacting a compound of formula III wherein $L^1$ and $L^2$ are suitable ligands with a compound of formula IIIb, in which X represents a leaving group, in the presence of a catalyst.

Suitable values for X include, for example, halogen such as bromo or iodo, and a trifluoromethanesulphonyloxy group. Suitable values for the ligands $L^1$ and $L^2$ present on the boron atom include groups independently selected from hydroxy, (1–4C)alkoxy (such as methoxy or ethoxy) and (1–6C)alkyl (such as methyl, ethyl, propyl or butyl). The groups $L^1$ and $L^2$ may, together with the boron atom to which they are attached, form a boroxin ring. Further suitable values for $L^1$ and $L^2$ include those in which L1 and L2 together with the boron atom to which they are attached form a cyclic borate ester group. Thus, for example, the groups $L^1$ and $L^2$ may be joined together to define an —oxyalkyleneoxy— or —oxyalkyleneaminoalkyleneoxy— group so that $L^1$ and $L^2$ together with the boron atom define a cyclic borate ester group. As a particular example, the group —$BL^1L^2$ may represent a dialkanolamine boronic ester group, a specific example of which is a N-methyl-0, 0-diethanolamine borate ester group. A particularly suitable leaving group is the group —$B(OH)_2$.

Suitable catalysts include, for example, a catalyst selected from a palladium (0), palladium (II), nickel (0) and nickel (II) catalyst. Particular catalysts include, tetrakis-(triphenylphosphine)nickel(0), bis(triphenylphosphine)nickel(II) chloride, nickel(II)chloride, palladium(II)chloride, bis(triphenylphosphine)palladium(II)chloride, bis(triphenylphosphine)phenylpalladium iodide and tetrakis(triphenylphosphine)palladium(0). A radical initiator, for example, azo(bisisobutyronitrile) may also be present.

The process is generally performed in the presence of a suitable solvent or diluent, for example, a hydrocarbon, such as toluene or xylene, or an ether such as dioxan or tetrahydrofuran, and at a temperature in the range, for example, 20°–150° C.

Compounds of formula III may be prepared by reaction of a compound of formula RO—$BL^1(L^2)$, such as a compound of formula $B(OR)_3$, wherein R is (1–6C)alkyl with a Grignard Reagent or phenyllithium compound derived from a compound of formula IV in which X is halogen such as bromo in an analogous manner to the preparation of compounds of formula V mentioned below.

Alternatively, compounds of formula III in which $R^1$ is hydroxy and $R^2$ is hydrogen may be prepared by reaction of quinuclidin-3-one with a Grignard Reagent or phenyllithium compound derived, using standard procedures such as those mentioned in (a) above, from a compound of formula IIIa in which "hal" represents halogen such as bromo or iodo and $L^1$ and $L^2$ are as defined above, and in which they are preferably joined together so that —$BL^1L^2$ is a cyclic borate ester group. The compounds of formula IIIa in which $R^1$ is hydroxy and $R^2$ is hydrogen may be converted into those in which $R^1$ and $R^2$ are both hydrogen or $R^1$ and $R^2$ are joined together so that $CR^1$—$CR^2$ is a double bond using standard procedures such as those mentioned under (d), (e), (f) or (g) below.

(c) Reacting a compound of formula IV in which X is a suitable leaving group with a compound of formula V in which $L^1$ and $L^2$ are suitable ligands in the presence of a catalyst.

Suitable values for X, $L^1$ and $L^2$, suitable catalysts and suitable reaction conditions are those mentioned under (b) above.

The compounds of formula V may be prepared by reaction of a boron compound of formula RO—$BL^1(L^2)$ in which $L^1$ and $L^2$ are alkyl or alkoxy groups as defined above with a compound of formula $Ar^2$—M wherein M is a metal such as Li or a derivative such as —MgBr. Thus, for example, a compound of formula $B(OR)_3$ wherein R is a (1–6C)alkyl group may be reacted with a Grignard Reagent or phenyllithium compound derived, using standard procedures such as those mentioned in (a) above, from a compound of formula $Ar^2$—hal wherein "hal" represents a halogeno atom such as bromo or iodo. The reaction is generally carried out in a solvent such as tetrahydrofuran or diethyl ether, or a mixture thereof, and at a temperature −78° C. to 25° C. The compounds of formula V wherein the ligands attached to boron are alkoxy may be converted to those in which the ligands are hydroxy by hydrolysis using standard techniques. The boroxin compounds may be prepared from the latter by dehydration using standard procedures.

The compounds of formula IV in which $R^1$ is hydroxy and $R^2$ is hydrogen may be prepared by reaction of quinuclidin-3-one with a phenyllithium compound derived, using procedures such as those analogous to those mentioned under (a) above, from a compounds of formula IVa in which "hal" represents a halogen atom such as bromo or iodo and X is as defined above. The compounds of formula IV in which $R^1$ is hydroxy and $R^2$ is hydrogen may be converted into compounds of formula IV in which $R^1$ and $R^2$ are both hydrogen using standard procedures such as those mentioned in (d) or (g) below, and into compounds in which $R^1$ and $R^2$ are joined so that $CR^1$—$CR^2$ is a double bond using standard procedures such as those mentioned in (e) or (f) below.

(d) For those compounds of formula I in which $R^1$ and $R^2$ are both hydrogen, reducing a compound of formula I in which $R^1$ and $R^2$ are joined together so that —$CR^1$—$CR^2$ is a double bond.

The reduction may be carried out, for example, by catalytic hydrogenation, or by reaction with a suitable reducing agent. Suitable reaction conditions include, for example, catalytic hydrogenation using a catalyst which comprises a noble metal. Particular catalysts include palladium, platinum, nickel and supported catalysts such as Pd/C. The reduction is conveniently carried out in a solvent of, for example, an alcohol such as ethanol, and at (or near) ambient temperature and optionally under pressure.

Further suitable reaction conditions include, for example, reduction with a borane such as diborane. The reaction is generally carried out in an inert solvent of, for example, tetrahydrofuran or methyl t-butyl ether at, for example, a temperature of 0° to 60° C. It may be preferable to cool the reaction below ambient temperature (e.g. to about 0° C.) during the reduction. The borane generated may be hydrolysed by treatment with an organic acid such as acetic acid.

(e) For those compounds of formula I in which $R^1$ and $R^2$ are joined together so that $CR^1$—$CR^2$ is a double bond, dehydrating a compound of formula I in which $R^1$ is hydroxy.

The dehydration may be carried out using an acid such as sulphuric acid (for example, concentrated sulphuric acid), or p-toluene sulphonic acid. The reaction may conveniently be carried out with heating. For example, the reaction may be carried out using p-toluene sulphonic acid in a hydrocarbon solvent of, for example, toluene or xylene at ambient temperature to reflux, and preferably at reflux. The dehydration may also be carried out using trifluoroacetic acid in an inert solvent such as dichloromethane and at a temperature from ambient temperature to the reflux temperature of the reaction mixture.

(f) For compounds of formula I in which $R^1$ and $R^2$ are joined together so that $CR^1$—$CR^2$ is a double bond, treating a compound of formula VI in which X is a leaving group with a base.

Suitable values for X include, for example, halogeno such as chloro, bromo or iodo, or a sulphonyloxy group such as methanesulphonyloxy or toluenesulphonyloxy. Suitable bases include alkali metal hydroxides (such as potassium or sodium hydroxide), and alkali metal alkoxides (such as potassium t-butoxide or sodium ethoxide).

The reaction may conveniently be carried out in the presence of a solvent, preferably a polar organic solvent. Suitable solvents include, for example, an alcohol (such as ethanol), or an aprotic solvent such as dimethylformamide or N-methyl pyrrolidone. The reaction may be carried out at ambient temperature or at an elevated temperature such as at temperature between ambient and the reflux temperature of the reaction mixture.

The compounds of formula VI may be prepared, for example, from compounds of formula I in which $R^1$ is hydroxy and $R^2$ is hydrogen using methods well known in the art. For example, compounds of formula VI in which X is halogen may be prepared by reaction of formula I in which $R^1$ is hydroxy with the appropriate phosphorus halide (for example $PCl_3$, $PBr_3$ or $PI_3$) or, where X is chloro, by reaction with thionyl chloride. Compounds of formula VI in which X is methane sulphonyloxy or toluenesulphonyloxy may be prepared by reaction of the compound of formula I in which R is hydroxy with mesyl chloride or tosyl chloride respectively (g) For those compounds of formula I in which $R^1$ and $R^2$ are both hydrogen, by dehydroxylation of a compound of formula I in which $R^1$ is hydroxy.

The reaction may be carried out by catalytic hydrogenation. Suitable reaction conditions include those mentioned under (d) above. The reaction may also be carried out using, for example, trifluoroacetic acid and $Et_3SiH$, conveniently at a temperature between ambient temperature and the reflux temperature of the reaction mixture (e.g. at about 50° C.).

It will be appreciated that in some of the reactions mentioned herein it may be necessary/desirable to protect any sensitive groups in the compounds. The instances where protection is necessary or desirable and suitable methods for protection are known to those skilled in the art. Thus, if reactants include groups such as amino, carboxy or hydroxy it may be desirable to protect the group in some of the reactions mentioned herein. Suitable protecting groups for hydroxy include, for example, silyl groups such as trimethylsilyl or t-butyldimethylsilyl, tetrahydropyranyl and esterifying groups such as a methyl or ethyl ester; and for amino groups include benzyloxycarbonyl and t-butoxycarbonyl. Carboxy groups may be protected in a reduced form such as in the form of the corresponding protected alcohol, which may be subsequently oxidised to give the carboxy group. The protecting groups may be removed at any convenient stage in the synthesis using conventional techniques well known in the chemical art.

It will also be appreciated that the preferred process for preparing a particular compound of formula I will depend upon the nature of the various radicals. Similarly, the preferred choice of reagent will depend upon the nature of the various radicals present. For example, when it is required to reduce a particular compound the reducing agent will generally be selected to be one which does not interfere with other groupings present.

It will also be appreciated that certain of the various optional substituents in the compounds of the present invention may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acylhalide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halogeno group. Particular examples of modifications include the reduction of a nitro group to an amino group by for example, catalytic hydrogenation with a nickel catalyst or treatment with iron in the presence of hydrochloric acid with heating; oxidation of alkylthio to alkylsulphinyl or alkylsulphonyl.

When a pharmaceutically-acceptable salt of a compound of the formula I is required, it may be obtained, for example, by reaction of said compound with the appropriate acid (which affords a physiologically acceptable anion), or with the appropriate base (which affords a physiologically acceptable cation), or by any other conventional salt formation procedure.

As mentioned previously, the compounds of the formula I (and their pharmaceutically-acceptable salts) are inhibitors of the enzyme squalene synthase. Thus the compounds of the present invention are capable of inhibiting cholesterol biosynthesis by inhibition of de novo squalene production.

The beneficial pharmacological properties of the compounds of the present invention may be demonstrated using one or more of the following techniques.

(a) Inhibition of Squalene synthase

In this test, the ability of a compound to prevent the formation of squalene from a radioactive substrate (tritiated farnesyl pyrophosphate) is assessed.

The test compound is incubated at a concentration of 25 micromolar in 200 μl of a buffered solution containing potassium phosphate (50 mM), $MgCl_2$ (4.95 mM), KF (9.9 mM), NADPH (0.9 mM) and rat liver microsomal protein (20 μg). Rat liver microsomes are prepared by the method described in published European Patent Application No. 324,421 and stored in liquid nitrogen prior to assay. Assay vials are kept at 37° C. throughout the incubation.

The reaction is started with the addition of the substrate (1-[$^3$H]-farnesyl pyrophosphate), final concentration 20 μM, and stopped after 15 minutes reaction time with the addition of 50 μl of 4% KOH. The reaction products are separated from unreacted substrate after application to a C-18 octadecyl 1 ccBond column (Analytichem Int product No. 617101). An aqueous fraction is eluted with 250 μl of 0.1M KOH. Squalene is then eluted with 1.0 ml 10% ethylacetate in hexane and radioactivity determined. The difference in radioactivity in the presence and absence of the test compound is used to determine the level of inhibition. If the test compound inhibits at greater than about 70% at 25 micromolar, it is generally re-tested at 25 and 2.5 micromolar. The $IC_{50}$ (concentration which results in a 50% inhibition of squalene production), of the test compound can be determined by testing the compound at several, for example five, concentrations predicted from the two concentration results. The $IC_{50}$ can then be determined from a plot of percentage inhibition against concentration of test compound.

In general, compounds of formula I show significant inhibition in the above test at a concentration in the range of about 0.001 to 25 μM.

By way of illustration of the squalene synthase inhibitory properties of the compounds of formula I, the compound described in Example 2 below gave an $IC_{50}$ of 0.24 μM; and the compound described in Example 4 gave about 54% inhibition at a concentration of 2.5 μM.

(b) Ache rat cholesterol synthesis assay.

This is an acute in vivo test in the rat to measure de novo hepatic cholesterol synthesis from exogenously administered $^{14}$C-acetate.

Female rats (35–55 g) are housed in reverse lighting conditions (red light from 0200h–1400h) for a period of about 2 weeks prior to test. Animals are allowed free access to chow and drinking water throughout this period. At test, animals should weigh 125–150 g.

Test compounds may be administered by oral gavage, dissolved or suspended in 0.5% polysorbate, or by ip or iv dosing. Control animals receive vehicle alone. After 1 hour the rats are injected ip with 25 μCi [2-$^{14}$C]-acetate (NEN DUPONT. specific activity, 45–60 mCi/mmol NEC-085H, or AMERSHAM specific activity, 50–60mCi/mmol CFA 14) in a volume of 0.25 ml saline (100 μCi/ml). After a further hour, rats are terminally anaesthetised with halothane and a blood sample obtained from the abdominal vena cava.

1 ml of plasma is lyophilised and then saponified in 2 ml ethanolic KOH (1 part 33% KOH, 9 parts ethanol) at 75° C. for 2 hours. After addition of an equal quantity of water, non-saponifiable lipids are extracted with two 5 ml volumes of hexane. The hexane extracts are evaporated to dryness and the residues dissolved in ethanol to determine cholesterol specific radioactivity. $ED_{50}$ values can be determined in the standard way.

In general, compounds of formula I show activity in the range of about 0.1 to 100 mg/kg.

By way of illustration, the compound of formula I described in Example 2 gave an $ED_{50}$ of 14 mg/kg; and the compound described in Example 4 gave an $ED_{50}$ of 4.5 mg/kg.

No overt toxicity was detected when compounds of the formula I were administered at several multiples of their minimum inhibitory dose or concentration.

As mentioned above, the compounds of the present invention are squalene synthase inhibitors and hence possess the property of inhibiting cholesterol biosynthesis. Thus the compounds of the present invention will be useful in treating diseases or medical conditions in which an inhibition of squalene synthase is desirable, for example those in which a lowering of the level of cholesterol is blood plasma is desirable. In particular, the compounds of the present invention will be useful in treating hypercholesterolemia and/or ischaemic diseases associated with atheromatous vascular degeneration such as atherosclerosis. The compounds of the present invention will also be useful in treating fungal infections.

Thus according to a further feature of the present invention there is provided a method of inhibiting squalene synthase in a warm-blooded animals (such as man) requiring such treatment, which method comprises administering to said animal an effective amount of a compound of formula I (as herein defined), or a pharmaceutically-acceptable salt thereof. In particular, the present invention provides a method of inhibiting cholesterol biosynthesis, and more particularly to a method of treating hypercholesterolemia and atheromatous vascular degeneration (such as atherosclerosis).

Thus the present invention also provides the use of a compound of formula I (as herein defined), or a pharmaceutically-acceptable salt thereof, for the manufacture of a medicament for treating diseases or medical conditions in which a lowering of the level of cholesterol in blood plasma is desirable (such as hypercholesterolemia and atherosclerosis).

When used in the treatment of diseases and medical conditions in which an inhibition of cholesterol biosynthesis is desired, for example in the treatment of hypercholesterolemia or atherosclerosis, it is envisaged that a compound of formula I (or a pharmaceutically acceptable salt thereof) will be administered orally, intravenously, or by some other medically acceptable route so that a dose in the general range of, for example, 0.01 to 50 mg per kg body weight is received. However it will be understood that the precise dose administered will necessarily vary according to the nature and severity of the disease, the age and sex of the patient being treated and the route of administration.

In general, the compounds of formula I (or a pharmaceutically-acceptable salt thereof) will usually be administered in the form of a pharmaceutical composition, that is together with a pharmaceutically acceptable diluent or carrier, and such a composition is provided as a further feature of the present invention.

A pharmaceutical composition of the present invention may be in a variety of dosage forms. For example, it may be in the form of tablets, capsules, solutions or suspensions for oral administration, in the form of a suppository for rectal administration; in the form of a sterile solution or suspension for parenteral administration such as by intravenous or intramuscular injection.

A composition may be obtained by conventional procedures using pharmaceutically acceptable diluents and carriers well known in the art. Tablets and capsules for oral administration may conveniently be formed with a coating, such as an enteric coating (for example, one based on cellulose acetate phthalate), to minimise dissolution of the active ingredient of formula I (or a pharmaceutically-acceptable salt thereof) in the stomach or to mask unpleasant taste.

The compounds of the present invention may, if desired, be administered together with (or sequentially to) one or more other pharmacological agents known to be useful in the treatment of cardiovascular disease, for example, together with agents such as HMG-CoA reductase inhibitors, bile acid sequestrants, other hypocholesterolaemic agents such as fibrates, for example gemfibrozil, and drugs for the treatment of coronary heart disease. As a further example, the compounds of the present invention may, if desired, be administered together with (or sequentially to) an angiotensin converting enzyme (ACE) inhibitor, such as captopril, lisinopril, zofenopril or enalapril.

The compounds of the present invention may also find utility as antifungal agents, and so the present invention also provides a method of treating fungal infections which comprises administration to an a warm blooded animal, such as man, in need of such treatment an effective amount of a compound of formula I, or a pharmaceutically acceptable salt thereof. When used in this way the compounds of the present invention may, in addition to the formulations mentioned above, be adapted for topical administration and such a composition is provided as a further feature of the present invention. Such compositions may be in a variety of forms, for example creams or lotions.

The invention will now be illustrated by the following non-limiting Examples in which, unless otherwise stated:

(i) evaporations were carried out by rotary evaporation in vacuo (ii) operations were carried out at room temperature, that is in the range 18°–26° C.;

(iii) yields are given for illustration only and are not necessarily the maximum attainable by diligent process development;

(iv) proton NMR spectra were normally determined at 200 MHz in deuterated dimethyl sulphoxide as solvent, using tetramethylsilane (TMS) as an internal standard, and are expressed as chemical shifts (delta values) in parts per million relative to TMS using conventional abbreviations for designation of major peaks: s, singlet; m, multipier; t, triplet; br, broad; d, doublet;

(v) all end-products were characterised by microanalysis, NMR and/or mass spectroscopy; and (vi) conventional abbreviations are used for individual radicals and recrystallisation solvents, for example, Me=methyl, Et=ethyl, Pr=Propyl, $Pr^i$=isopropyl, Bu=butyl, $Bu^i$=isobutyl, Ph=phenyl; EtOAc=ethyl acetate, $Et_2O$=ether, MeCN=acetonitrile, MeOH=methanol, EtOH=ethanol, $Pr^iOH$=2-propanol, $H_2O$=water.

EXAMPLE 1

A solution of tert-butyllithium (14 ml of a 1.7M solution in pentane) was added over a period of 15 minutes to a stirred solution of 4-(pyrid-3-yl)bromobenzene (2.0 g) in freshly distilled dry tetrahydrofuran (50 ml) at −70° C. and under an atmosphere of argon. The resulting reaction mixture was stirred at −70° C. for a further 2 hours. A solution of quinuclidin-3-one (1.0 g) in freshly distilled tetrahydrofuran (5 ml) was then added and the reaction mixture stirred at −70° C. for 30 minutes. The reaction mixture was then allowed to warm to ambient temperature and stirred for a further 17 hours. 2M aqueous hydrochloric acid (50 ml) and ice were added, and the mixture partitioned with ethyl acetate (3×20 ml). The separated aqueous layer was basified using 2M sodium hydroxide solution and ice, and the resulting aqueous mixture extracted with ethyl acetate (4×50 ml). The ethyl acetate extracts were combined, dried ($MgSO_4$) and evaporated to yield a gum (0.61 g) which was purified by column chromatography on silica gel (Merck Art 7734) using a 50:50:1 volume/volume mixture of methanol: ethyl acetate: ammonium hydroxide as eluent. There was thus obtained a gum which was crystallised from ethyl acetate to afford 3-[4-(pyrid-3-yl)phenyl]quinuclidin-3-ol as a colourless solid (127 mg), m.p. 172°–173° C.; microanalysis, found: C, 74.5; H, 7.1; N, 9.9%; $C_{18}H_{20}N_2O.0.5H_2O$ requires: C, 74.7; H, 7.2; N, 9.7%; NMR ($[CD_3]_2SO$): 1.3–1.5(3H, m), 2.0 (1H, m), 2.1–2.3(1H, m), 2.6–2.9(4H, m), 2.95(1H, d), 3.45(1H, d), 5.2(1H, s), 7.4–7.5(1H, m), 7.6–7.7(4H, m), 8.0–8.1(1H, m), 8.6(1H, d of d) and 8.9(1H, d); m/Z: 281 (M+H).

The 4-(pyrid-3-yl)bromobenzene used as starting material was obtained as follows:

(a) A cold (about 0° C.) solution of sodium nitrite (8.97 g) in distilled water (20 ml) was added slowly to a stirred suspension of p-bromoaniline (22 g) in a mixture of concentrated hydrochloric acid (55 ml) and distilled water (55 ml) whilst maintaining the temperature of the reaction mixture at −5° C. The reaction mixture was filtered and pyridine (69 g) was then added to the stirred filtrate whilst cooling with an ice-bath. The mixture was stirred at 0° C. for 1 hour and then allowed to warm to ambient temperature and stirred for a further 48 hours. The reaction mixture was then poured into 4M hydrochloric acid (200 ml) and the resulting mixture washed with ethyl acetate (3×50 ml). The aqueous phase was basified using 2M sodium hydroxide solution and extracted with ethyl acetate (6×50 ml). The ethyl acetate extracts were combined, dried ($MgSO_4$) and evaporated. The residue was purified by column chromatography on silica gel (Merck Art 7734) using a 10:90 volume/volume mixture of methanol: ethyl acetate as eluent. There was thus obtained:

4-(pyrid-2-yl)bromobenzene (3.7 g) as a solid, m.p. 64°–65° C.; NMR ($CDCl_3$): 7.25 (1H, m), 7.6 (2H, m), 7.7(2H, m), 7.9(2H, m) and 8.7(1H, d);

4-(pyrid-3-yl)bromobenzene (1.2 g) as an oil, NMR ($CDCl_3$): 7.3–7.5(3H, m), 7.6(2H, d), 7.85(1H, d of t), 8.6(1H, d of d) and 8.8(1H, d); and 4-(pyrid-4-yl)bromobenzene (0.82 g) as a solid, m.p. 123°–124° C.; NMR ($CDCl_3$): 7.45–7.52(4H, m), 7.62(2H, m) and 8.65(2H, m).

In a further embodiment, 4-(pyrid-3-yl)bromobenzene was obtained as follows:

(b) A solution of 4-bromobenzeneboronic acid (6.0 g) in absolute ethanol (15 ml) was added slowly to a stirred mixture of a solution of 3-bromopyridine (4.7 g) in toluene (30 ml), a saturated aqueous solution of sodium carbonate (10 ml) and tetrakistriphenylphosphine palladium [0] (1.0 g) under an atmosphere of argon. The mixture was then heated to reflux and stirred at reflux under an atmosphere of argon for 6 hours. The mixture was cooled and water (50 ml) added. The resulting mixture was extracted with ethyl acetate (3×30 ml). The ethyl acetate extracts were combined, and then extracted with 2M aqueous hydrochloric acid (3×20 ml). The acidic extracts were combined, cooled by the addition of ice and basified by the addition of sodium hydroxide solution (1.35 $g.cm^{-3}$) to give a pH of 9. The mixture was then extracted with ethyl acetate (3×30 ml). These ethyl acetate extracts were combined, dried (MgSO$_4$) and evaporated to afford 4-(pyrid-3-yl)bromobenzene as a colourless oil (1.2 g); NMR (CDCl$_3$): 7.3–7.5 (3H, m), 7.6(2H, d), 7.85(1H, d of t), 8.6(1H, d of d) and 8.8(1H, d).

EXAMPLE 2

The procedure described in Example 1 was repeated but using 4-(pyrid-2-yl)bromobenzene (0.94 g) in place of 4-(pyrid-3-yl)-bromobenzene to give 3-[4-(pyrid-2-yl)phenyl]quinuclidin-3-ol as a solid (0.35 g), m.p. 237°–238° C.; microanalysis, found: C, 75.7; H, 7.1; N, 9.5%; C$_{18}$H$_{20}$N$_2$O.0.25H$_2$O requires: C, 75.9; H, 7.2; N, 9.8%; NMR ([CD$_3$]$_2$SO): 1.3–1.5(3H, m), 2.0(1H, s), 2.1–2.25(1H, m), 2.6–2.9(4H, m), 2.95(1H, d), 3.45(1H, d), 5.2(1H, s), 7.3(1H, m), 7.65(2H, d), 7.8–8.0(2H, m), 8.05(2H, d) and 8.65(1H, d).

The 4-(pyrid-2-yl)bromobenzene used as starting material was obtained as described in Example 1, part (a).

EXAMPLE 3

A solution of t-butyl lithium in pentane (2.5 ml, 1.75M) was added dropwise to a stirred solution of 4-(pyrid-4-yl)bromobenzene (0.5 g) in freshly distilled (from CaH$_2$) tetrahydrofuran (15 ml) at −70° C. and under an atmosphere of argon. The reaction mixture was stirred at −70° C. for 5 minutes, and a solution of quinuclidin-3-one (0.25 g) in freshly distilled (from CaH$_2$) tetrahydrofuran (3 ml) was then added. The reaction mixture was stirred at −70° C. for a further 3 hours and then at ambient temperature for 17 hours. Saturated aqueous ammonium chloride solution (50 ml) was added and the tetrahydrofuran was removed by evaporation. The residue was acidified with 2M aqueous hydrochloric acid and the mixture was washed with ethyl acetate (3×30 ml). The aqueous mixture was basified with aqueous sodium hydroxide solution (density, 1.35 g/cm$^3$) and extracted with ethyl acetate (4×30 ml). The ethyl acetate extracts were combined, dried (MgSO$_4$) and evaporated to give an oil which was purified by preparative thin layer chromatography on silica gel (Schleicher & Schull preparative silica gel plates, G1505/LB254, 40×20×0.5 mm) using a 50:50:1 (v/v/v) mixture of ethyl acetate, methanol and concentrated ammonium hydroxide as eluent to give 3-[4-(pyrid-4-yl)phenyl]quinuclidin-3-ol as a solid; microanalysis, found: C, 72.7; H, 7.2; N, 8.8%; C$_{18}$H$_{20}$N$_2$O. H$_2$O, requires: C, 72.5; H, 7.4; N,9.3%; NMR ([CD$_3$)$_2$SO): 1.5(1H,m), 1.7(1H,m), 2.4(2H,s), 3.1–3.3(4H,m), 3.4(2H,d), 3.85(2H,d), 7.4–7.8(6H,m) and 8.6(2H,d of d); m/z 281(M+H).

The 4-(pyrid-4-yl)bromobenzene used as starting material was prepared using the procedure described in Example 1(b) for the preparation of 4-(pyrid-3-yl)bromobenzene, but using 4-bromopyridine in place of 3-bromopyridine. There was thus obtained 4-(4-bromophenyl)pyridine as a solid (31% yield), m.p. 123°–124° C.; microanalysis, found: C, 56.4; H, 3.4; N, 5.9%; C$_{11}$H$_8$NBr requires: C, 56.4; H, 3.4; N, 6.0%; NMR([CD$_3$]$_2$SO): 7.65–7.8(6H, m) and 8.65–8.70(2H,m); m/z 235(M+H).

EXAMPLE 4

A solution of sec-butyl lithium in cyclohexane (15 ml, 1.3M) was added slowly to a stirred solution of 4-bromophenylbenzeneboronic acid [N-methyl-O,O-diethanolamine]ester (2.84 g) in freshly distilled tetrahydofuran (50 ml) at 31 100° C. and under an atmosphere of argon. The reaction mixture was stirred at −100° C. for 30 minutes, whereon a grey precipitate was formed. A solution of quinuclidin-3-one (1.25 g) in tetrahydrofuran (10 ml) was added slowly to the reaction mixture and the mixture stirred at −100° C. for 10 minutes. The reaction mixture was allowed to warm to ambient temperature and then stirred for a further 2 hours. An aqueous solution of ammonium chloride (1.1 g in 10 ml of water) was added to the reaction mixture and the mixture stirred for 30 minutes. The tetrahydrofuran was removed by evaporation. A saturated aqueous solution of sodium carbonate (20 ml) was added, followed by toluene (40 ml). A solution of 5-bromopyrimidine (1.59 g) in absolute ethanol (20 ml) was added to the mixture. The reaction vessel was then purged with argon and tetrakistriphenylphosphine palladium [0] (200 mg) was added to the reaction mixture with stirring. The reaction mixture was heated at reflux whilst under an atmosphere of argon for 6 hours. The reaction mixture was stirred at ambient temperature overnight and the solvent was then removed by evaporation. Ice was added to the residue followed by 2M aqueous hydrochloric acid (100 ml) and the aqueous mixture was extracted with toluene (3×50 ml). The aqueous phase was basified with ice/aqueous sodium hydroxide solution (density, 1.35 g/cm$^3$) and extracted with methylene chloride (4×100 ml). The methylene chloride extracts were combined, dried (MgSO$_4$) and evaporated to give an oil which was triturated with ethyl acetate to give a solid which was washed with acetonitrile to give 3-[4-(pyrimidin-5-yl)phenyl]quinuclidin-3-ol, (30% yield), m.p. 184°–185° C.; microanalysis, found: C, 71.5; H, 6.9; N, 14.3%; C$_{17}$H$_{19}$N$_3$O. 0.25H$_2$O, requires: C, 71.5; H, 6.9; N, 14.7%; NMR([CD$_3$)$_2$SO): 1.2–1.5(3H,m), 2.0(1H,br.d), 2.1–2.2(1H,m), 2.6–2.8(4H, m), 2.9(1H, d), 3.4(1H,d), 5.2(1H,s), 7.6–7.8(4H, d of d), 9.15(2H,s), 9.2(1H,s); m/z 282(M+H).

The 4-bromophenylbenzeneboronic acid [N-methyl-O,O-diethanolamine]ester used as starting material was prepared using the method described in Tett. Lett.,30(51), (1989), 7194 as follows.

A mixture of 4-bromophenylboronic acid (5.0 g) and N-methyldiethanolamine (2.95 g) in freshly distilled tetrahydrofuran (50 ml) was stirred at ambient temperature for 1 hour. The solvent was removed by evaporation to give an oil which was treated with dichloromethane (3×50 ml) and evaporated to give 4-bromophenylboronic acid [N-methyl-O,O-diethanolamine]ester as a solid (98% yield), m.p. 143°–144° C.; microanalysis, found: C, 46.5; H, 5.5; N, 4.8%; C$_{11}$H$_{15}$NO$_2$BBr requires: C, 46.5; H, 5.3; H, 4.9%; NMR([CD$_3$]$_2$SO): 2.2(3H,s), 2.9–3.0(2H,m), 3.2–3.3(2H, m), 3.8–4.0(4H,m), 7.35–7.45(4H,m); m/z 284(M+H).

EXAMPLE 5

The procedure described in Example 4 was repeated, but using 2-bromopyridimidine in place of 5-bromopyrimidine. There was thus obtained, after purification by column chromotography on silica gel (Merck Art 7734 ) using a 50:50:1 (v/v/v) mixture of methanol:ethyl acetate:ammonium hydroxide as eluent to give 3-4-(pyrimidin-2-yl)-phenyl] quinuclidin-3-ol as a solid, m.p. 246°–7° C.; microanalysis, found: C, 71.7; H, 6.8; N, 14.9%; C$_{17}$H$_{19}$N$_3$O, requires: C, 71.4; H, 6.8; N, 14.7%; NMR ([CD$_3$]$_2$SO): 1.2–1.5(3H,m), 2.0(1H,br.d), 2.1–2.2(1H,m), 2.6–2.8(4H,m) 2.9(1H,d), 3.4 (1H,d), 5.25(1H,s), 7.4(1H,t), 7.65(2H,d), 8.35(2H,d) and 8.9(2H,d); m/z 282(M+H).

EXAMPLE 6

The procedure described in Example 4 was repeated, but using 3-bromo-4-methylpyridine in place of 5-bromopyrimidine. There was thus obtained, after purification by column chromatography on silica gel (Merck Art 7734) using methanol as eluent, 3-[4-(4-methylpyrid-3-yl)phenyl]quinuclidin-3-ol as a solid foam; microanalysis, found: C, 71.6; H, 7.7; N, 8.4%; $C_{19}H_{22}N_2O$, 1.67 $H_2O$ requires: C, 71.7; H, 7.8; N, 8.8%; NMR($[CD_3]_2SO$): 1.2–1.5 (3H,m), 2.0(1H,s), 2.1–2.2(1H,m), 2.3(3H,s), 2.6–2.85(4H,m), 2.9(1H,d), 3.4(1H,d), 5.2(1H,s), 7.35–7.4(2H,d), 7.6–7.65(2H,d), 8.35(1H,s), 8.42(1H,s) and 8.45(1H,s); m/z 295(M+H).

EXAMPLE 7

The procedure described in Example 4 was repeated, but using ethyl-3-bromopicolinate in place of 5-bromopyrimidine. There was thus obtained, after purification by column chromatography on silica gel (Merck Art 7734) using methanol as eluent, 3-[4-(5-ethoxycarbonylpyrid-3-yl)phenyl]quinuclidin-3-ol as a solid, m.p. 150°–151° C. microanalysis found: C, 70 4; H, 6 7; N 7.4%; $C_{21}H_{24}N_2O_3$, 0.25 $H_2O$ requires: C, 70.7; H, 6.9; N, 7.8%; NMR($[CD_3]_2SO$): 1.3–1.5 (6H,m), 2.0(1H,s), 2.1–2.2(1H,m), 2.6–2.8 (4H, m), 2.9(1H,d), 3.4(1H,d), 4.4(2H,q), 5.2(1H,s), 7.65(2H,d), 7.75(2H,d) 8.5(1H,t), 9.05(1H,d), 9.15(1H,d); m/z 353(M+H).

EXAMPLE 8

The procedure described in Example 4 was repeated, but using 2-bromo-5-methylpyridine in place of 5-bromopyrimidine. There was thus obtained 3-[4-(5-methylpyrid-2-yl)phenyl]quinuclidin-3-ol which was purified by preparative thin layer chromatography on silica gel (Schleicher & Schull preparative silica gel plates, G1505/LS254, 40×20× 0.5 mm) using methanol as eluent to give a foam, m/z 295(M+H).

EXAMPLE 9

The procedure described in Example 4 was repeated but using 2-chloropyrazine in place of 5-bromopyrimidine. There was thus obtained, after purification on silica gel (Merck Art. 7734) using methanol as eluent, 3-[4-(pyrazin-2-yl)phenyl]quinuclidin-3-ol as a white solid, m.p. 195°–196° C.; microanalysis found: C, 71.9; H, 7.2; N, 14.5%; $C_{17}H_{19}N_3O0.1$ $H_2O$ requires: C, 71.6; H, 6.8; N, 14.7%; NMR($[CD_3]_2SO$): 1.2–1.5(3H,m); 2.0(1H,s); 2.1–2.2(1H,m); 2.6–2.9(5H,m); 2.9(1H,d); 3.4(1H,d); 5.2(1H,brs); 7.7(2H,d); 8.15(2H,d); 8.6(1H,d); 8.75(1H,d); 9.25(1H,d); m/z 282(M+H).

EXAMPLE 10

The procedure described in Example 4 was repeated but using 3-chloro-6-methylpyridazine in place of 5-bromopyrimidine. There was thus obtained, after purification on silica gel (Merck Art. 7734) using methanol as eluent, 3-[4-(6-methyl-pyridazin-3-yl)phenyl]-quinuclidin-3-ol as a solid, m.p. 192°–193° C. microanalysis found: C, 71.0; H, 7.4; N,12.5%; $C_{18}H_{21}N_3O$ (0.5 diethyl ether, 0.25 $H_2O$) requires: C, 71.3; H, 7.9; N, 12.5% ; NMR($[CD_3]_2SO$): 1.2–1.5(3H,m); 2.0(1H, br d); 2.1–2.2(1H,m); 2.6–2.8(7H, m +s); 2.9(1H,d); 3.4(1H,d); 5.2(1H,brs); 7.6–7.7(3H,d of t); 8.05–8.15(3H,d of t); m/z 296(M+H).

EXAMPLE 11

Illustrative pharmaceutical dosage forms suitable for presenting the compounds of the invention for therapeutic or prophylactic use include the following tablet and capsule formulations, which may be obtained by conventional procedures well known in the art of pharmacy and are suitable for therapeutic or prophylactic use in humans:

| | mg/tablet |
|---|---|
| (a) Tablet I | |
| Compound Z* | 1.0 |
| Lactose Ph. Eur. | 93.25 |
| Croscarmellose sodium | 4.0 |
| Maize starch paste (5% w/v aqueous paste) | 0.75 |
| Magnesium stearate | 1.0 |
| (b) Tablet II | mg/tablet |
| Compound Z* | 50 |
| Lactose Ph. Eur | 223.75 |
| Croscarmellose sodium | 6.0 |
| Maize starch | 15.0 |
| Polyvinylpyrrolidone (5% w/v aqueous paste) | 2.25 |
| Magnesium stearate | 3.0 |
| (c) Tablet III | mg/tablet |
| Compound Z* | 100 |
| Lactose Ph. Eur. | 182.75 |
| Croscarmellose sodium | 12.0 |
| Maize starch paste (5% w/v aqueous paste) | 2.25 |
| Magnesium stearate | 3.0 |
| (d) Capsule | mg/capsule |
| Compound Z* | 10 |
| Lactose Ph. Eur. | 488.5 |
| Magnesium stearate | 1.5 |

Note
*The active ingredient Compound Z is a compound of formula I, or a salt thereof, for example a compound of formula I described in any of the preceding Examples.

The tablet compositions (a)–(c) may be enteric coated by conventional means, for example, with cellulose acetate phthalate.

CHEMICAL FORMULAE

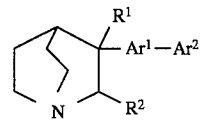   I

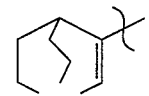   Ia

M-Ar¹ — Ar²   II hal-Ar¹ — Ar²   IIa
$H_2N$ — Ar¹-hal   IIb

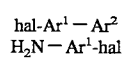   IIc

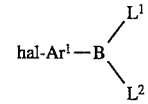   III

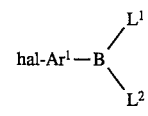   IIIa

Ar² — X   IIIb

-continued
CHEMICAL FORMULAE

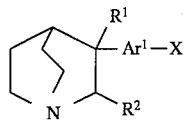 IV

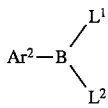 IVa

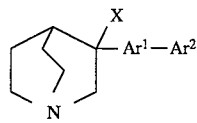 V

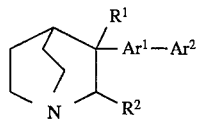 VI

I claim:

1. A compound of formula I, or a pharmaceutically acceptable salt thereof,

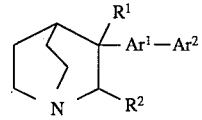

wherein:

$R^1$ is hydrogen or hydroxy;

$R^2$ is hydrogen; or $R^1$ and $R^2$ are such that $>CR^1CR^2<$ is of the structure $>C=C<$;

$Ar^1$ is a phenylene moiety;

$Ar^2$ is a 6-membered heteroaryl moiety containing one or two nitrogen atoms;

and wherein $Ar^1$ and $Ar^2$ are independently substituted or unsubstituted with one or more substituted independently selected from halogeno, hydroxy, amino, nitro, cyano, carboxy, carbamoyl, (1–6C)alkyl, (2–6C)alkenyl, (2–6C)alkynyl, (1–6C)alkoxy, (1–6C)alkylamino, di-[(1–6C)alkyl]amino, N-(1–6C)alkylcarbamoyl, di-N,N-[(1–6C)alkyl]carbamoyl, (1–6C)alkoxycarbonyl, di-N,N-[(1–6C)alkylcarbamoyl, (1–6C)alkoxylcarbonyl, (1–6C)alkylthio, (1–6C)alkylsulphinyl, (1–6C)alkylsulphonyl, halogeno(1–6C)alkyl, (1–6C)alkanoylamino, (1–4C)alkylenedioxy, (1–6C)alkanoyl and oxime derivatives thereof and 0-(1–6C)alkyl ether of said oxime derivatives.

2. A compound as claimed in claim 1 wherein $R^1$ is hydrogen or hydroxy; $R^2$ is hydrogen; or $R^1$ and $R^2$ are joined together so that $CR^1$—$CR^2$ is a double bond; $Ar^1$ is 1,3-phenylene or 1,4-phenylene; $Ar^2$ is a pyridyl, pyrimidinyl, pyrazinyl or pyridazinyl; and wherein one or both of $Ar^1$ and $Ar^2$ may optionally bear one or more substituents independently selected from hydroxy, amino, nitro, cyano, carboxy, carbamoyl, fluoro, chloro, bromo, iodo, methyl, ethyl, propyl, isopropyl, butyl, isobutyl, sec-butyl, allyl, prop-1-enyl, but-2-enyl, 2-methyl-2-propenyl, prop-2-ynyl, but-2-ynyl, methoxy, ethoxy, propoxy, isopropoxy, butoxy, methylamino, ethylamino, propylamino, butylamino, dimethylamino, diethylamino, methylpropylamino, dipropylamino, N-methylcarbamoyl, N-ethylcarbamoyl, N-propylcarbamoyl, N,N-dimethylcarbamoyl, N,N-diethylcarbamoyl, methoxycarbonyl, ethoxycarbonyl, propoxycarbonyl, methylthio, ethylthio, propylthio, isopropylthio, butylthio, methylsulphinyl, ethylsulphinyl, propylsulphinyl, isopropylsulphinyl, butylsulphinyl, methylsulphonyl, ethylsulphonyl, propylsulphonyl, isoproylsulphonyl, butylsulphonyl, trifluoromethyl, difluoromethyl, fluoromethyl, methylenedioxy, ethylenedioxy, formamido, acetamido, propionamido, iso-propionamido, butyramido, iso-butyramido, formyl, acetyl, propionyl, butyryl, or a group of formula —C(Ra)=NOH or —C(Ra)=NORb in which Ra is hydrogen, methyl, ethyl, propyl, isopropyl or butyl, and Rb is methyl, ethyl, propyl, isopropyl or butyl.

3. A compound as claimed in claim 1 or 2 wherein $Ar^1$ is 1,4-phenylene.

4. A compound as claimed in claim 1 or 2 wherein $R^1$ is hydroxy and $R^2$ is hydrogen.

5. A compound as claimed in claim 1 or 2 wherein $Ar^2$ is 2-pyridyl, 3-pyridyl, 4-pyridyl, 2-pyrimidinyl, 5-pyrimidinyl, 2-pyrazinyl or 3-pyridazinyl.

6. A compound as claimed in claim 1 or 2 wherein one or both of $Ar^1$ and $Ar^2$ may optionally bear one or more substituents independently selected from halogeno, hydroxy, amino, nitro, cyano, carboxy, carbamoyl, (1–6C)alkyl, (1–6C)alkoxy, (1–6C)alkylamino, di-[(1–6C)alkyl]carbamoyl, (1–6C)alkoxycarbonyl, (1–6C)alkylthio, (1–6C)alkylsulphinyl, (1–6C)alkylsulphonyl, halogeno (1–6C)alkyl and (1–6C)alkanoylamino.

7. A compound of formula I, or a pharmaceutically acceptable salt thereof,

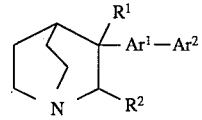

wherein:

$R^1$ is hydrogen or hydroxy;

$R^2$ is hydrogen; or $R^1$ and $R^2$ are joined together so that $CR^1$—$CR^2$ is a double bond;

$Ar^1$ is a phenylene moiety;

$Ar^2$ is a 6-membered heteroaryl moiety containing one or two nitrogen atoms;

and wherein one or both of $Ar^1$ and $Ar^2$ may optionally bear one or more substituents independently selected from halogeno, hydroxy, amino, nitro, cyano, carboxy, carbamoyl, (1–6C)alkyl, (1–6C)alkoxy, (1–6C)alkylamino, di-[(1–6C)alkyl]carbamoyl, (1–6C)alkoxycarbonyl, (1–6C)alkylthio, (1–6C)alkylsulphinyl, (1–6C)alkylsulphonyl, halogeno (1–6C)alkyl and (1–6C)alkanoylamino.

8. A compound as claimed in claim 7 wherein $R^1$ is hydroxy; $R^2$ is hydrogen; and $Ar^1$ is 1,4-phenylene.

9. A compound as claimed in claim 1 which is selected from the group consisting of:

3-[4-(6-methyl-pyridazin-3-yl)phenyl]quinuclidin-3-ol;
3-[4-(pyrazin-2-yl)phenyl]quinuclidin-3-ol;
3-[4-(5-methylpyrid-2-yl)phenyl]quinuclidin-3-ol;
3-[4-(5-ethoxycarbonylpyrid-3-yl)phenyl]quinuclidin-3-ol;
3-[4-(4-methylpyrid-3-yl)phenyl]quinuclidin-3-ol;
3-[4-(pyrimidin-2-yl)phenyl]quinuclidin-3-ol;
3-[4-(pyrimidin-5-yl)phenyl]quinuclidin-3-ol;
3-[4-(pyrid-3-yl)phenyl]quinuclidin-3-ol;
3-[4-(pyrid-4-yl)phenyl]quinuclidin-3-ol; and
3-[4-(pyrid-2-yl)phenyl]quinuclidin-3-ol;

or a pharmaceutically acceptable salt thereof.

10. A pharmaceutical composition which comprises a compound of formula I, or a pharmaceutically acceptable salt thereof, as claimed in claim 1 together with a pharmaceutically acceptable diluent or carrier.

11. A method of inhibiting cholesterol biosynthesis in a warm-blooded animal in need thereof, said method comprising administering to said animal an effective amount of a compound of formula I:

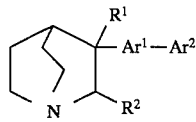

wherein:

$R^1$ is hydrogen or hydroxy;

$R^2$ is hydrogen; or $R^1$ and $R^2$ are such that $>CR^1CR^2<$ is of the structure $>C=C<$;

$Ar^1$ is a phenylene moiety;

$AR^2$ is a 6-membered heteroaryl moiety containing one or two nitrogen atoms;

and wherein $Ar^1$ and $Ar^2$ are independently substituted or unsubstituted with one or more substituents independently selected from halogeno, hydroxy, amino, nitro, cyano, carboxy, carbamoyl, (1–6C)alkyl, (2–6C)alkenyl, (2–6C)alkynyl, (1–6C)alkoxy, (1–6C)alkylamino, di-[(1–6C)alkyl]amino, N-(1–6C)alkylcarbamoyl, di-N,N-[(1–6C)alkyl]carbamoyl, (1–6C)alkoxycarbonyl, (1–6C)alkylthio, (1–6C)alkylsulphinyl, (1–6C)alkylsulphonyl, halogeno(1–6C)alkyl, (1–6C)alkanoylamino, (1–4C)alkylenedioxy, (1–6C)alkanoyl and oxime derivatives thereof and 0-(1–6C)alkyl ethers of said oxime derivatives.

12. A method of treating hypercholesterolemia or atheromatous vascular degeneration in a warm-blooded animal, said method comprising administering to said animal in need thereof an effective amount of a compound of formula I:

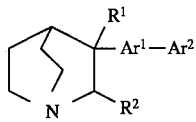

wherein:

$R^1$ is hydrogen or hydroxy;

$R^2$ is hydrogen; or $R^1$ and $R^2$ are such that $>CR^1CR^2<$ is of the structure $>C=C<$;

$Ar^1$ is a phenylene moiety;

$AR^2$ is a 6-membered heteroaryl moiety containing one or two nitrogen atoms;

and wherein $Ar^1$ and $Ar^2$ are independently substituted or unsubstituted with one or more substituents independently selected from halogeno, hydroxy, amino, nitro, cyano, carboxy, carbamoyl, (1–6C)alkyl, (2–6C)alkenyl, (2–6C)alkynyl, (1–6C)alkoxy, (1–6C)alkylamino, di-[(1–6C)alkyl]amino, N-(1–6C)alkylcarbamoyl, di-N,N-[(1–6C)alkyl]carbamoyl, (1–6C)alkoxycarbonyl, (1–6C)alkylthio, (1–6C)alkylsulphinyl, (1–6C)alkylsulphonyl, halogeno(1–6C)alkyl, (1–6C)alkanoylamino, (1–4C)alkylenedioxy, (1–6C)alkanoyl and oxime derivatives thereof and 0-(1–6C)alkyl ethers of said oxime derivatives.

13. A method of treating a fungal infection in a warm-blooded animal, said method comprising administering to said animal in need thereof an effective amount of a compound of formula I:

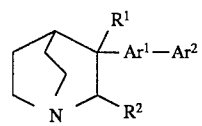

wherein $R^1$ is hydrogen or hydroxy;

$R^2$ is hydrogen; or $R^1$ and $R^2$ are such that $>CR^1CR^2<$ is of the structure $>C=C<$;

$Ar^1$ is a phenylene moiety;

$Ar^2$ is a 6-member heteroaryl moiety containing one or two nitrogen atoms;

and wherein $Ar^1$ and $Ar^2$ are independently substituted or unsubstituted with one or more substituents independently selected from halogeno, hydroxy, amino, nitro, cyano, carboxy, carbamoyl, (1–6C)alkyl, (2–6C)alkenyl, (2–6C)alkynyl, (1–6C)alkoxy, (1–6C)alkylamino, di-[(1–6C)alkyl]amino, N-(1–6C)alkylcarbamoyl, di-N,N-[(1–6C)alkyl]carbamoyl, (1–6C)alkoxycarbonyl, (1–6C)alkylthio, (1–6C)alkylsulphinyl, (1–6C)alkylsulphonyl, halogeno(1–6C)alkyl, (1–6C)alkanoylamino, (1–4C)alkylenedioxy, (1–6C)alkanoyl and oxime derivatives thereof and 0-(1–6C)alkyl ethers of said oxime derivatives.

* * * * *